United States Patent [19]
Silverberg

[11] Patent Number: 5,063,919
[45] Date of Patent: Nov. 12, 1991

[54] PROTECTIVE SLEEVE

[76] Inventor: Doris C. Silverberg, 508 Coeur de Royale, Apt. 403, St. Louis, Mo. 63141

[21] Appl. No.: 403,087

[22] Filed: Sep. 5, 1989

[51] Int. Cl.$^5$ .............................................. A61F 13/00
[52] U.S. Cl. .......................................... 128/82; 2/59; 2/22; 2/16
[58] Field of Search ................... 2/16, 59, 76, 22, 240, 2/311, 312; 36/110; 128/82, 157, 158; 24/72.7, 102 A, 131 R, 573.1

[56] References Cited

U.S. PATENT DOCUMENTS

| | | | |
|---|---|---|---|
| 396,945 | 1/1889 | Michelson | 2/240 |
| 814,328 | 3/1906 | Russell | 24/102 A |
| 1,093,032 | 4/1914 | Cadenas | 2/240 |
| 1,172,622 | 2/1916 | Minkos | 2/240 |
| 1,194,627 | 8/1916 | Hill | 2/59 |
| 1,237,865 | 8/1917 | Brown | 2/240 X |
| 1,299,574 | 4/1919 | Hofto | 2/59 |
| 1,353,592 | 9/1920 | Howard | 2/240 X |
| 1,517,984 | 12/1924 | Harvey | 2/59 |
| 1,616,699 | 2/1927 | Mitchell | 24/102 A |
| 1,651,437 | 12/1927 | Bochonok | 24/102 A |
| 1,980,486 | 11/1934 | King et al. | 128/82 X |
| 2,244,871 | 6/1941 | Guirnzburg | 2/59 |
| 2,493,878 | 1/1950 | Kirtz | 2/61 |
| 2,582,648 | 1/1952 | Mowbray | 128/82 X |
| 2,854,670 | 10/1958 | Naccash | 2/76 X |
| 3,329,144 | 7/1967 | Liman | 128/82 |
| 3,416,518 | 12/1968 | Samuels et al. | 128/82 |
| 3,657,741 | 4/1972 | Blanco | 2/59 |
| 3,735,759 | 5/1973 | MacKay | 128/82 |
| 3,741,203 | 6/1973 | Liman | 128/82 |
| 3,747,125 | 7/1973 | Goldman et al. | 128/82 X |
| 3,785,374 | 1/1974 | Lipson | 128/82 |
| 3,824,998 | 7/1974 | Snyder | 128/157 |
| 4,036,220 | 7/1977 | Bellasalma | 128/82 |
| 4,043,326 | 8/1977 | Little et al. | 128/82 |
| 4,069,515 | 1/1978 | Swallow et al. | 2/239 |
| 4,098,268 | 7/1978 | Scott | 128/82 |
| 4,229,930 | 10/1980 | Ostermaier | 24/72.7 X |
| 4,287,608 | 9/1981 | Meyer | 2/16 |
| 4,523,586 | 6/1985 | Couri | 128/82 |
| 4,530,350 | 7/1985 | Brown et al. | 128/82 |
| 4,562,834 | 1/1987 | Bates et al. | 128/82 |
| 4,639,945 | 2/1987 | Betz | 128/82 X |
| 4,651,354 | 3/1987 | Petrey | 2/239 |
| 4,722,143 | 2/1988 | Everett | 128/82 X |
| 4,727,864 | 3/1988 | Wiesenthal et al. | 128/82 |
| 4,768,501 | 9/1988 | George | 128/157 X |
| 4,911,151 | 3/1990 | Rankin et al. | 128/82 |

FOREIGN PATENT DOCUMENTS

| | | | |
|---|---|---|---|
| 0230775 | 8/1987 | European Pat. Off. | 2/69.5 |
| 895388 | 9/1953 | Fed. Rep. of Germany | 24/102 |
| 839704 | 6/1960 | United Kingdom | 24/72.7 |

OTHER PUBLICATIONS

Caba Watergard Package, front and back, claiming rights under U.S. Pat. No. 4,562,834, Bates et al.
Dr. Leonard's Health Care Catalog, Spring 1989, p. 18 discloses water proof covering.
St. Louis Medical Supply 1990 Catalog, p. 30, Shower Shield Cast Protectors.
Shower Shield Package, front and back as illustrated in item AS.
The Journal of the American Medical Association, vol. 117, No. 18, Date: Nov. 1, 1941.

*Primary Examiner*—Werner H. Schroeder
*Assistant Examiner*—Jeanette E. Chapman
*Attorney, Agent, or Firm*—Heller & Kepler

[57] ABSTRACT

A water proof member protects casts, splints, or other appliances or surgical dressings from water damage. A combination of a securing member and straps secure the member and provide a water proof seal between the water proof member and the wearer.

19 Claims, 2 Drawing Sheets

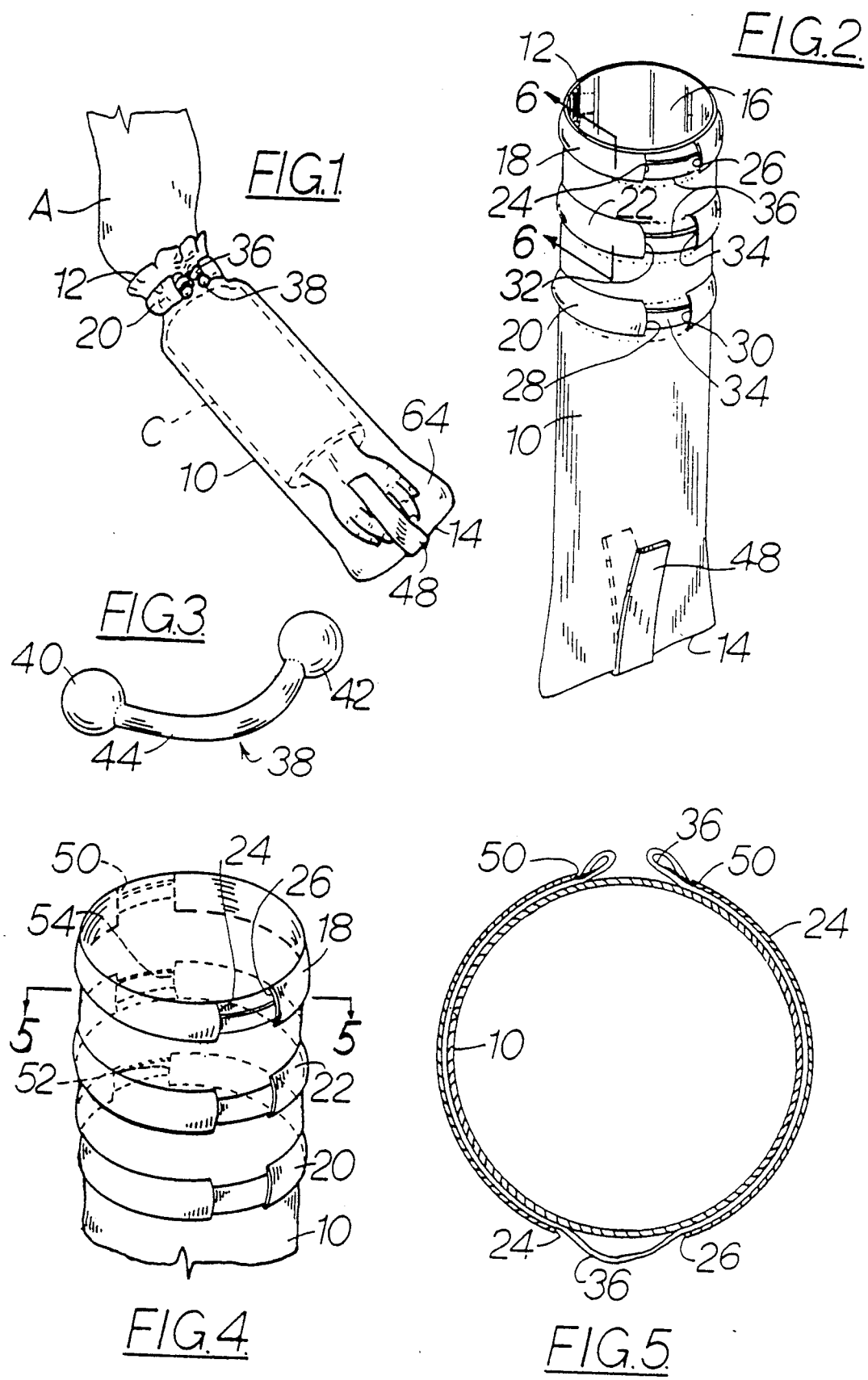

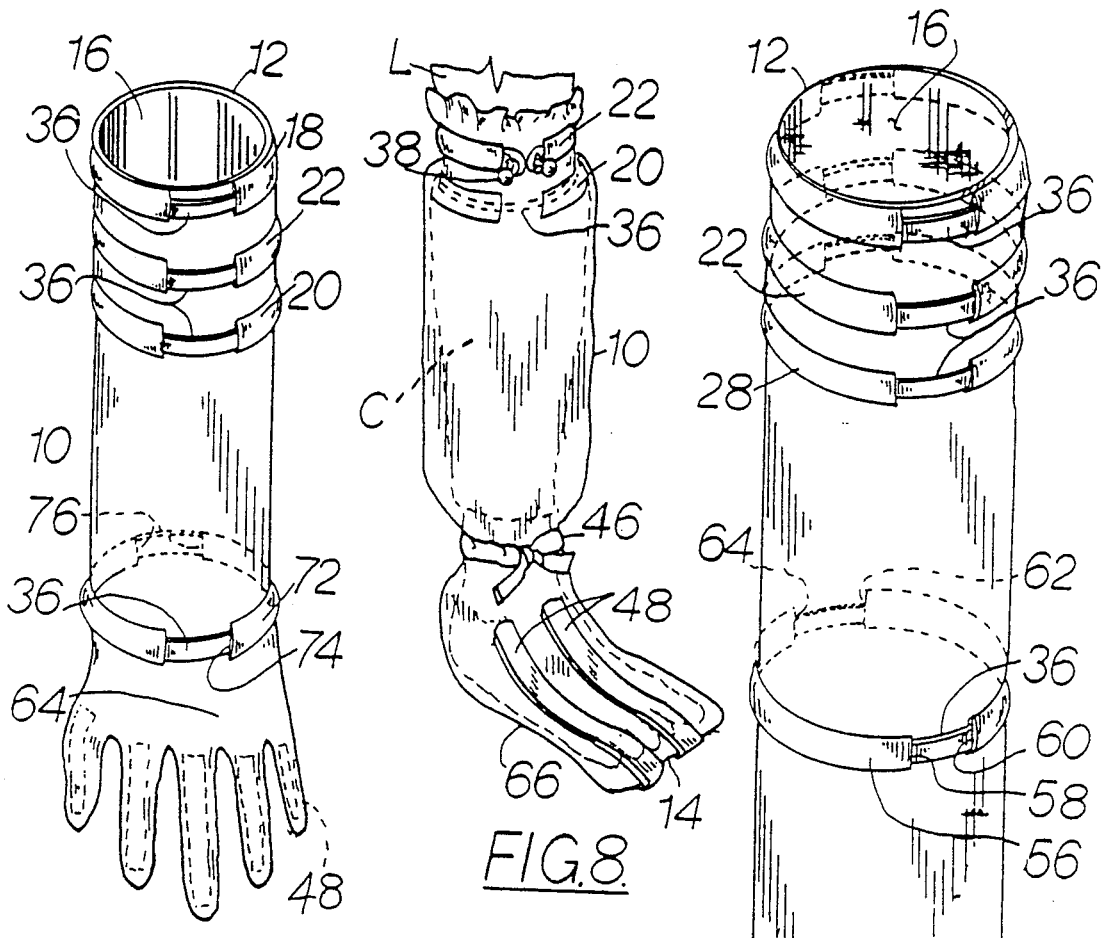
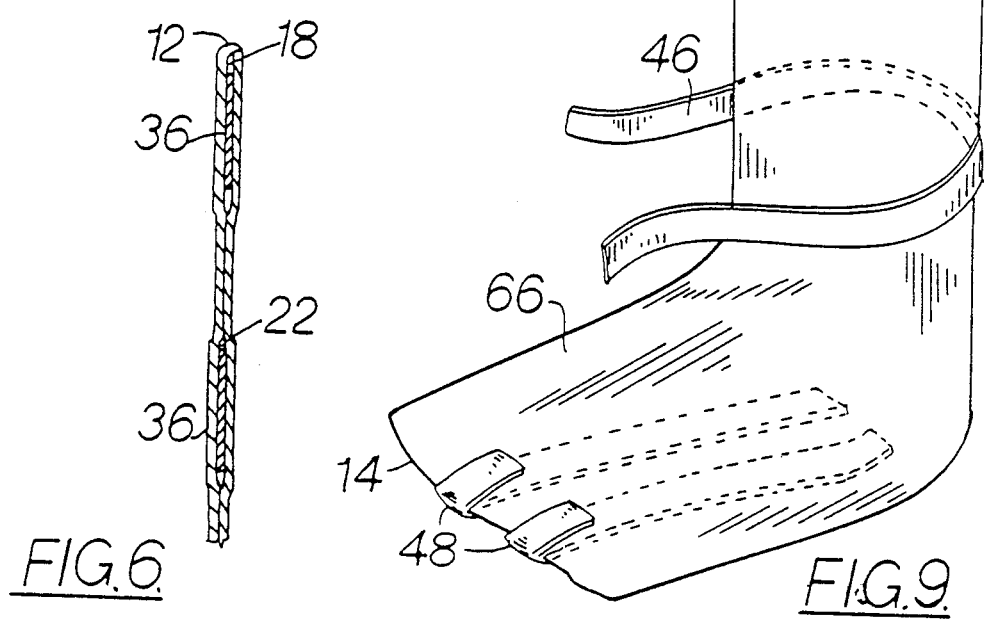

PROTECTIVE SLEEVE

BACKGROUND OF THE INVENTION

The present invention relates in general to protect casts from damage during extended wear and pertains, more particularly, to a cast protector for a person with a plaster cast, a splint, or a surgical dressing. The cast protector of this invention is an improvement over the conventional elasticized sleeves, bags or other waterproof covers. A water proof member protects casts, splints, or other appliances or surgical dressings from water damage. A combination of a securing member and straps secure the member and provide a water proof seal between the water proof member and the wearer.

With the conventional protector it is generally necessary to tape, tie, or otherwise provide a seal between an open end of a sleeve protector and the skin of the user. For example, it is common to provide a waterproof covering or sleeve with an opening at one end for receiving an arm or a leg and the opposite end closed to so as to cover the hand or foot of the user. The open end typically includes an elastic closure member. Tape may be applied to the elastic in an attempt to ensure that the opening is sealed in a water tight manner.

Another drawback associated with the conventional protectors or sleeves is their tendency to be too tightly wrapped. The primary purpose of the sleeve is to allow someone in a cast or a splint, surgical dressing or other bandage or appliance, the luxury of bathing during the period of convalescence. The sleeves are often intended to be put on only when needed. The fastening members are subject to more than average wear and tear. The fastening members are often designed to over-compensate so as to guarantee a water proof seal. Thus, the conventional sleeves provide a closure that is often too tight. This results in the fastener acting like a tourniquet and the sleeve becomes uncomfortable and potentially damaging to the wearer as it may interfere with the healing process.

The number of injuries requiring casts or splints is staggering. It is estimated that in one year there may be as many as eight million or more injuries including fractures or dislocations in the United States alone, with as many as five million lower extremity and toe related injuries and three million upper extremity and finger related injuries. It is strongly believed that a functional, easy to use and inexpensive, reusable protective sleeve will allow many injured people to endure the necessary period of their convalescence.

Accordingly, it is an object of the present invention to provide an improved protective sleeve to protect casts from damage during extended wear. With the protective sleeve of this invention it is expected that individuals requiring protection for a plaster cast, a splint, or a surgical dressing will be gratified by the increased activity allowed, particularly for bathing and showering.

Another object of the present invention is to provide an improved protective sleeve that can be worn while performing normal activities or tasks allowed by the particular dressing or cast. It is expected that normal activity will in all probability be curtailed do to the injury.

A further object of the present invention is to provide an improved protective sleeve that can be adjusted to fit the wearer and the area that is to be protected. A unique closing system provides the water proof closure desired for arms or legs. The closing system allows various sizes of individuals to use the protective sleeve.

Still another object of the present invention is to provide an improved protective sleeve that can be readily reused. It is felt that, like crutches, a family could reuse the protective sleeve at least once under normal conditions. This feature reduces the cost to the user and his or her family.

Still a further object of the present invention is to provide an improved protective sleeve that provides frictional surfaces on a walking portion or a handling portion. With the additional walking or handling capabilities of this invention, the careful, prudent user is provided a range of activities not found with conventional apparatus or devices intended for the same or similar purpose.

Another object of the present invention is to provide an improved protective sleeve that can be readily modified for use by changing the length of the sleeve to fit the intended use.

SUMMARY OF THE INVENTION

To accomplish the foregoing and other objects of this invention there is provided a protective sleeve for protecting an extremity of a user when the extremity requires a plaster cast, a splint, or a surgical dressing. The protective sleeve comprises a wearable member including means for protecting the extremity. The protective sleeve defines a receiving cavity for the extremity. The protective sleeve of this invention further includes means for providing an adjustable and secure sleeve about the extremity and in combination with fastening means secures the protective sleeve. The secured protective sleeve provides a substantially water proof seal about the extremity. The protective sleeve generally includes a generally tubular member having an open end and a closed end. The generally tubular member defines the cavity for receiving the extremity of the user. In an embodiment of the present invention at least one channel is located proximate the extremity receiving cavity. The channel receives an adjustable securing means for securing protecting means about the extremity and effectively sealing the extremity receiving cavity against water or moisture. The protective sleeve of a preferred embodiment of the tubular member may include one or more channels. The securing means may include a continuous elastic securing band inserted in one channel in a single thickness or doubled up and inserted in one channel such that opposing end loops, formed by the doubling up of the band, protrude from one pair of opposing channel openings of the channel receiving the elastic securing band. The fastening means may include a generally dumb bell shaped member having opposing protuberances connected by an intermediate and possibly arcuate shaft member. In a preferred embodiment the fastening means is inserted under the elastic band member which is in turn tightened on the fastening means in an over and under weaving pattern until the desired tightness is obtained. Enlarged portions of the fastening means provide for holding the band in place and in the desired condition of tightness. In another embodiment the englarged portions or protuberances receive associated and opposing ends of securing means which have been doubled up in the respective channels or passageways in order to provide end loops which assist to fasten the securing means in place with a desired and an adjustable tension.

The closed end of the generally tubular protective sleeve may form a generally foot-shaped portion or a glove-shaped portion depending on the extremity covered by the protective sleeve. Either the foot-shaped portion or glove-shaped portion may also include a non-skid rubber or other friction strip. In an embodiment of this invention an elastic strap tied about an ankle portion of the individual and on the outside of the protective sleeve secures the protective sleeve in order to impede the protective sleeve from creeping down over the heel and foot of the individual while walking with the protective sleeve in place over a lower extremity and foot portion.

These and other objects and features of the present invention will be better understood and appreciated from the following detailed description of embodiments thereof, selected for purposes of illustration and shown in the accompanying drawings.

BRIEF DESCRIPTION OF THE DRAWINGS

FIG. 1 is a perspective view of a protective sleeve in use in accordance with the present invention;

FIG. 2 is another perspective view of the protective sleeve depicted in FIG. 1;

FIG. 3 is a perspective view of a securing device in accordance wit the present invention;

FIG. 4 is a partial perspective view of another embodiment of a protective sleeve in accordance with the present invention;

FIG. 5 is a sectional view taken along line 5—5 in FIG. 4;

FIG. 6 is a cross-sectional view taken along line 6—6 in FIG. 2;

FIG. 7 is a perspective view of another embodiment of the protective sleeve for use on an arm in accordance with the present invention;

FIG. 8 is a perspective view of another embodiment of the protective sleeve for use on a leg in accordance with the present invention; and FIG. 9 is a perspective view of another embodiment of the protective sleeve for use on a leg.

DETAILED DESCRIPTION

Referring now to the drawings there is shown preferred embodiments for the protective sleeve of this invention. The protective sleeve is described in connection with a cast protector application for an arm and a leg. The protective sleeve of the present invention is particularly adapted for providing a water proof protector or sleeve which can be worn in a shower.

The drawings show the protective sleeve in conjunction with an arm and with a leg, each in a cast. The arm and leg embodiments of this invention will be described now, with like members having like reference numbers for the purpose of clarity and ease of understanding.

The protective sleeve generally includes a tubular member 10 with an open end 12 and a closed end 14. The tubular member defines a cast receiving cavity 16. The cavity 16 is intended to receive whatever cast, bandage, or dressing is required and being worn by a user.

Adjustability of the protective sleeve is provided by one or more passage means intended for receiving a securing means and held with a desired and adjustable tightness with a fastening means. While one passage is sufficient the preferred embodiments of this invention will have more than a single passage means. In this way the length of the protective sleeve may be adjusted simply by removing a portion of the tubular member 10. This shortens the sleeve and provides a better fit.

In the illustrated embodiments three channels are shown. An upper passage means or channel 18 is located proximate the open end 12 of the tubular member 10. A lower channel 20 is located intermediate the upper channel 18 and the closed end 14 of the tubular member 10. An intermediate channel 22 is provided between the upper channel 18 and the lower channel 20.

Openings must be provided in the channels to receive the securing means. The upper channel 18 is provided with a pair of opposing openings, a first opening 24 and a second opening 26. The lower channel 20 is provided with another pair of opposing openings, a first opening 28 and a second opening 30. The intermediate channel 22 is also provided with a pair of opposing openings, a first opening 32 and a second opening 34.

A securing means is provided to secure the protective sleeve to the extremity of the user. The securing means is received by the passage means and then fastened in an adjustable manner as further discussed below. The securing means is preferably an elastic member 36.

A preferred embodiment is illustrated in the section depicted in FIG. 6 showing a single thickness elastic member. A Penrose Drain also has been found to be suitable for use as the elastic member 36.

Another preferred embodiment is illustrated in FIG. 5, with respect to a posterior opening, in which the securing member is doubled up so as to form loops.

Referring again to the preferred embodiments illustrated in the drawing figures, a tightening and securing member 38 is provided to tighten and secure the securing means in the desired passage means or channel to suit the length of the extremity receiving the protective sleeve. The member 38 has a first knob or protuberance 40, a second knob or protuberance 42, and a shaft 44 intermediate knobs 40 and 42.

The illustrated embodiments, as discussed above, show a protective sleeve intended for use over an arm and a protective sleeve intended for use over a foot and a portion of a leg. Either of the protective sleeves may include an additional elastic securing means or strap 46, not received by any of the passage means, rather tied about an ankle portion of the individual and on the outside of the protective sleeve. This provides for securing the respective protective sleeve in order to impede the sleeve from creeping down over a heel and a foot portion of the individual while walking with the protective sleeve otherwise secured in place over the lower extremity and including the foot portion.

A feature of this invention is provided by the strategic placement of friction members. Use of either a foot portion 66 or a glove portion 64 extending from or part of the closed end 14 of either illustrated embodiment of the present invention may be enhanced with the application of friction means such as a non-skid strip 48. One or two strips 48 are illustrated, and it will be understood that more than two strips may be applied as desired. The non-skid strip 48 or other friction or gripping producing means or member may be applied to the protective sleeve with a suitable adhesive or molded into the material of the protective sleeve.

The present invention is intended to provide an individual with a plaster cast, splint, surgical dressing, or other bandage the convenience of taking a shower or tub bath. It will be readily understood that the protective sleeve of this invention may be used to protect the cast of the like while performing other chores suitable for the convalescence of the user. Furthermore, if the wearer is in reasonably good health, then the task of putting on this invention should be capable of being performed by the user alone.

One preferred material for manufacture of the present invention includes a slightly curved protective sleeve 10 which is made of a flexible, water proof polyethylene-vinyl material.

It is estimated that a suitable material could be approximately 5 mil thick. It is further estimated that the average protective sleeve for use on an arm would measure approximately seven (7) inches in diameter and twenty-eight (28) inches in length.

Referring again to the preferred embodiments illustrated herein, proximate the top or open end of the tubular member or sleeve 10 is the upper channel 18, which is preferably approximately two (2) inches wide. Additional channels are spaced at approximately two (2) inch intervals. If an embodiment includes the additional channels 20 and 22, then they preferably located and spaced at approximately two (2) inch intervals below the upper channel 18.

The protective sleeve may be adjustable for various extremity lengths. The adjustment may be accomplished by removing an upper portion of the tubular member 10. Spacing the channels at particular intervals allows a desired length adjustment. It is suggested that length adjustment be accomplished by removing an upper portion of the tubular sleeve 10 while leaving approximately one-half (½) inch above the channel. It is believed that this will leave aproximately two (2) inches of the tubular member 10 above a cast, splint, dressing, or the like, in typical situations.

In preferred embodiments of the present invention, the opposing channel openings should be spaced apart a sufficient distance so as to allow easy attachment of the securing means to the fastening means. In a preferred embodiment, the opposing openings (e.g. 24, 26, 28, 30, and 32, 34) are spaced apart so as to provide an opening approximately three (3) inches wide.

The securing means or elastic member 36 is preferably a double layer, flat, continuous rubber band approximately one (1) by nineteen (19) inches. This band is preferably an elastic material similar to a surgical Penrose drain. It will be understood that the section ilustrted in FIG. 6 shows a typcial single thickness elastic securing member. It will be further understood by one skilled in the art that the Penrose drain member or its equivalent is readily substituted for the elastic member depicted in the drawing figures for purposes of illustration.

In operation, in connection with either the arm or leg application previously mentioned, the extremity with the cast, bandage, dressing, or the like is inserted into the receiving cavity 16 until the foot or glove extends into the complementary glove or foot portion (if provided) of the tubular member 10. The sleeve length is adjusted as required by removing the excess portion of the tubular member 10.

With particular reference to use of the protective sleeve in association with an arm, the elastic member 36 inserted into the appropriate channel 18, 20, or 22 secures the protective sleeve in place on the extremity. The elastic member is wrapped or woven around the knobs or protuberances of the tightening and securing member 38. The tightness of the elastic member 36 around the extremity may be varied to accommodate varying thicknesses of arms. This adjustable feature of the present invention prevents water from leaking into the cavity 16.

In a preferred embodiment the member 38 is approximately two and one-half (2½) inches long and the knobs are approximately one and one-half (1½) inches in diameter. The shaft portion 44 may be somewhat flexible or slightly arcuate in order to facilitate the weaving portion of the fastening procedure.

The elastic member 36 is one preferred embodiment is doubled in the channels and has opposing loops extending out of the opposing openings of the associated channels. The loops are illustrated relative to the posterior channel openings in FIG. 5 and the other figures illustrate a single band.

The single band will typically be installed during manufacture and the doubled embodiment may be applied after the channels are formed.

The elastic member is tightened by wrapping it around the shaft 44 is a weaving pattern in an over and under fashion. The elastic band or member 36 is tightened until the sleeve fits snugly around the extremity. The elastic member 36 then loops around the knob or protuberance one or more times until elastic member 36 will no longer stretch over the knob or protuberance 40 or 42. The tubular member 10 of the protective sleeve should now provide a water proof seal around the extremity. If a looped band embodiment is used, then the protuberances or otherwise enlarged portions may be initially inserted into a loop or loops.

The protective sleeve for an arm is preferably tightened on the outside portion of the arm. The protective sleeve may be provided with one or more posterior channel or passage means openings to facilitate placement and securing of the protective sleeve on the extremity. As illustrated in the drawings there may be provided a posterior upper passage means or channel opening 50, a posterior lower passage means or channel opening 52, and a posterior intermediate passage means or channel opening 54.

The hand inserts into a glove portion 64 if provided. This glove portion may be further provided with the friction strips 48 or other suitable means.

With respect to application of this invention in association with the lege of a user, the protective sleeve is put on in generally the same fashion as already described for the arm. A foot portion 66 receives the foot. This embodiment includes the friction strips 48 as illustrated. In one preferred embodiment these friction strips include two (2) rubber strips of flexible, non-skid rubber. The strips may be approximately one (1) inch wide, approximately twenty-six (26) inches long, and approximately one-sixteenth (1/16) of an inch thick. It is believed that these strips, if two or more are used, should be approximately six (6) inches apart and extend over the closed curved end 14 with its integral foot portion 66. The strips may extend over the closed, curved end and up opposing sides of the tubular member 10 as illustrated, approximately fifteen (15) inches apart. This arrangement should provide the desired friction or non-skid surface and allow a single protective member for either the right leg or the left leg.

The leg embodiment may provide for an additional foot adjustment. The adjustment is provided as further described. The protective sleeve is slipped over the foot until it feels comfortable to the user. The elastic securing means or strap 46 ties around the foot proximate the ankle. A knot, preferably a bow, is tied and the extra length of the ends removed in order that the loose ends do not get in the way. It is believed that an elastic strap three-quarters (¾) of an inch by twenty-four (24) inches will suffice, with the loose ends removed to approximately two (2) inches from the knot.

The length of the leg embodiment of this invention will be adjusted similarly to the arm embodiment. When shortened approximately two (2) inches should be left above the cast, splint, dressing, of the like. As an example of the size of this embodiment of the present invention, a medium size may be thirty two (32) inches in circumference and forty six (46) inches in length.

The leg and arm embodiments of the present invention may be enhanced by including an additional adjustment means. Knee passage means such as channel 56 and wrist passage means such as channel 72 may be provided, thereby allowing adjustment of the protective sleeve to fit over the foot or hand, respectively. The leg embodiment may further include knee passage means openings such as a pair of openings 58 and an opposing pair of openings 60. Also included may be a posterior passage means opening pair such as generally indicated by reference character 62. The arm embodiment may further include wrist passage means openings such as a pair of openings 74 and a posterior opposing opening pair 76. These passage means also receive an elastic member as previously described.

Used in association with an arm or a leg, this invention should be adjusted and secured with the tightening and securing member 38 on the outside or outer aspect of the limb in order to avoid injury to the chest or genital area. It will be understood that the present invention should be used only upon the advice of a physician with particular, although not sole, attention to potential circulatory problems. The present invention should not be used by anyone who could not remove the protective sleeve if left alone. A maximum time of use should be indicated by a physician if the protective sleeve is to be tightened to the maximum, but in any event it is believed that the protective sleeve should be worn for no more than ten (10) minutes.

While specific embodiments have been shown and described, many variations are possible. The particular shape and size of the protective sleeve, as well as the material of manufacture may vary to suit conditions and extremity of limb sizes. It is believed that sizes for both arm and leg models of this invention may be provided in a variety of sizes, such as extra small, small, medium, large, and extra large. In the described embodiments there have been included foot and glove portions. In a more simplified version of the invention, the tubular member 10 may be open at both ends (not shown) with at least one passage means at each end. This simplified embodiment could be used to cover a knee or elbow cast, splint, dressing, bandage or the like and secured at either end to keep out water, for example, during a shower or tub bath. A variety of materials in various shapes may be used. The tubular member may be provided in different shapes so long as a cavity is provided for the extremity, if a closed end embodiment, or an opening is provided if the open at both ends alternative embodiment.

Having described the invention in detail, those skilled in the art will appreciate that modifications may be made of the invention without departing from its spirit. Therefore, it is not intended that the scope of the invention be limited to the specific embodiments illustrated and described. Rather, it is intended that the scope of this invention be determined by the appended claims and their equivalents.

What is claimed is:

1. A wearable member for protecting an extremity of a user enclosed or otherwise associated with a cast, splint, a surgical dressing, or other bandage treatment, comprising:
    means for protecting an extremity, the extremity protecting means defining an extremity receiving cavity;
    means for securing the protecting means about the extremity, the securing means adjustable about the extremity of the user, and a securing means receiving means extending generally around the circumference of the protecting means;
    means for receiving the securing means, the receiving means associated with the extremity protecting means, the receiving means further defining access means for accessing the securing means in order to secure the extremity protecting means to the extremity of the user; and
    means for fastening securing means, the fastening means including a generally dumb bell shaped member having opposing protuberances connected by an intermediate shaft member, wherein the securing means wrap around the intermediate shaft and below the protuberances so as to fasten the securing means in place with a desired and adjustable tension.

2. A wearable member as set forth in claim 1 wherein means for protecting an extremity include a generally tubular member having an open end and a closed end, the tubular member defining a cavity for receiving an extremity of an individual with a plaster cast, a splint, or a surgical dressing.

3. A wearable member as set forth in claim 1 wherein adjustable securing means and fastening means comprise:
    at least one channel located proximate extremity receiving means for receiving a securing means for securing the tubular member about the extremity;
    securing means for securing the tubular member about the extremity; and
    fastening means for fastening the securing means received in the channel and providing a desired and adjustable tightness of the securing means about the extremity, the securing means and the fastening means cooperating so as to provide a substantially water proof seal between the extremity receiving means of the tubular member and the extremity.

4. A sleeve for protecting an extremity of a user when the extremity requires a plaster cast, a splint, or a surgical dressing, comprising:
    a tubular member with one closed end and having means therefore receiving an extremity to which has been applied a cast, splint, dressing or other treatment not generally intended to become wet while the associated injury or wound heals;
    one or more channels located proximate extremity receiving means for receiving a securing means for securing the tubular member about the extremity;
    securing means for securing the tubular member about the extremity; and
    fastening means for fastening the securing means received in one of the associated channel and providing a desired and adjustable tightness of the securing means about the extremity, the fastening means including a generally dumb bell shaped member having opposing protuberances connected by an intermediate shaft member, wherein the securing means wrap around the intermediate shaft and below the protuberances so as to fasten the securing means in place with a desired and adjustable tension.

5. A sleeve as set forth in claim 4 wherein the tubular member further includes at least two channels, one channel located proximate to the open end of the sleeve, the one channel having at least one pair of opposing openings for receiving the securing means; and another channel located intermediate the one channel and the closed end of the tubular member, the other channel having at least one pair of opposing openings for receiving the securing means.

6. A sleeve as set forth in claim 5 wherein the tubular member further includes an intermediate channel located intermediate the one channel and the other channel, the intermediate channel having at least one pair of opposing openings for receiving the securing means.

7. A sleeve as set forth in claim 4 wherein the securing means includes a continuous elastic securing band doubled up and inserted in one channel such that opposing end loops formed by the doubling up of the band protrude from one pair of opposing channel openings of the channel receiving the elastic securing band.

8. A sleeve as set forth in claim 4 wherein the combination of fastening means and securing means comprise:
a tightening and securing member having a first knob, a second knob spaced apart from and connected to the first knob by a flexible intermediate shaft; and
the securing means includes a continuous elastic securing band doubled up and inserted in one channel such that opposing end loops formed by the doubling up of the band protrude from opposing channel opening pairs of the channel receiving the elastic securing band, such that the first knob inserts into one loop of the elastic band and the second knob inserts into the opposing loop of the elastic band for tightening the elastic band by successively wrapping the elastic band around the flexible intermediate shaft and over the knobs.

9. A protective sleeve as set forth in claim 4 wherein the closed end forms a generally foot-shaped portion.

10. A protective sleeve as set forth in claim 9 wherein the generally foot-shaped portion includes at least one non-skid rubber strip.

11. A protective sleeve as set forth in claim 9 wherein the sleeve includes an elastic strap tied about an ankle portion of the individual and on the outside of the sleeve, thereby securing the sleeve in order to impede the sleeve from creeping down over the heel and foot of the individual while walking with the sleeve in place over a lower extremity and foot portion.

12. A protective sleeve as set forth in claim 4 wherein the closed end forms a glove-shaped portion.

13. A protective sleeve as set forth in claim 9 wherein the generally glove-shaped portion includes at least one non-skid rubber strip.

14. A protective sleeve for protecting an extremity of a user when the extremity requires a plaster cast, a splint, or a surgical dressing, comprising:

a generally tubular member having an open end and a closed end, the tubular member defining a sleeve-like cavity for receiving an extremity of an individual with a plaster cast, a splint, or a surgical dressing;

an upper channel located proximate to the open end of the sleeve, the upper channel having a first anterior opening and a second anterior opening, the upper channel further including a first posterior opening and a second posterior opening;

a lower channel located intermediate the upper channel and the closed end of the sleeve, the lower channel having a first anterior opening and a second anterior opening, the lower channel further including a first posterior opening and a second posterior opening;

an intermediate channel located intermediate the upper channel and the lower channel, the intermediate channel having a first anterior opening and a second anterior opening, the intermediate channel further including a first posterior opening and a second posterior opening;

a continuous elastic securing band doubled up and inserted in one channel such that opposing end loops protrude form either first and second anterior openings or first and second posterior openings of the associated elastic securing band receiving channel; and a tightening and securing member having a first knob, a second knob spaced apart from and connected to the first knob by a flexible intermediate shaft, whereby the first knob is inserted into one loop of the elastic band and the second knob is inserted into the opposing loop of the elastic band and the elastic band is tightened by successively wrapping the elastic band over the flexible intermediate shaft and between and around the knobs to tighten the elastic band and provide a substantially water proof closure about the individual's extremity without excessively tightening the elastic band.

15. A protective sleeve as set forth in claim 14 wherein the closed end forms a generally foot-shaped portion.

16. A protective sleeve as set forth in claim 15 wherein the generally foot-shaped portion includes at least one non-skid rubber strip.

17. A protective sleeve as set forth in claim 16 wherein the sleeve includes an elastic strap tied about an ankle portion of the individual and on the outside of the sleeve, thereby securing the sleeve in order to impede the sleeve from creeping down over the heel and foot of the individual while walking with the sleeve in place over a lower extremity and foot portion.

18. A protective sleeve as set forth in claim 14 wherein the closed end forms a glove-shaped portion.

19. A protective sleeve as set forth in claim 18 wherein the generally glove-shaped portion includes at least one non-skid rubber strip.

* * * * *